US006294656B1

(12) United States Patent
Mittl et al.

(10) Patent No.: US 6,294,656 B1
(45) Date of Patent: Sep. 25, 2001

(54) TRANSFORMING GROWTH FACTOR β CRYSTALS

(75) Inventors: Peer Mittl, Maulburg (DE); Markus Grütter, Hochwald; Tudor Arvinte, Münchenstein, both of (CH)

(73) Assignee: Novartis Corporation, Basel (CH)

( * ) Notice: Subject to any disclaimer, the term of this patent is extended or adjusted under 35 U.S.C. 154(b) by 0 days.

(21) Appl. No.: 09/000,069

(22) PCT Filed: Jul. 17, 1996

(86) PCT No.: PCT/EP96/03140

§ 371 Date: Jan. 22, 1998

§ 102(e) Date: Jan. 22, 1998

(87) PCT Pub. No.: WO97/05166

PCT Pub. Date: Feb. 13, 1997

(30) Foreign Application Priority Data

Jul. 25, 1995 (EP) .................................................. 95810484

(51) Int. Cl.[7] ..................................................... A61K 38/18

(52) U.S. Cl. .............................. 530/399; 530/324; 514/12

(58) Field of Search ..................................... 530/324, 399; 514/12

(56) References Cited

U.S. PATENT DOCUMENTS

| | | | |
|---|---|---|---|
| 3,937,820 | 2/1976 | Mager et al. | 424/178 |
| 4,639,332 | 1/1987 | Grau | 530/303 |
| 4,850,966 | 7/1989 | Grau | 604/82 |
| 4,959,351 | 9/1990 | Grau | 514/4 |
| 5,322,933 | 6/1996 | Davies et al. | 530/399 |

FOREIGN PATENT DOCUMENTS

| | | |
|---|---|---|
| 1047919 | 2/1979 | (CA) . |
| 1155439 | 10/1983 | (CA) . |
| 1335924 | 6/1995 | (CA) . |
| 1126561 | 3/1962 | (DE) . |
| WO 95/09004 | 6/1995 | (WO) . |
| 8904742 | 6/1989 | (ZA) . |

OTHER PUBLICATIONS

Derwent Abstract of JP–07031875–A, 1995.*
"Adsorbent for TGF beta–1, useful for its determn.—consists of hydroxy apatite having a whisker– or needle–type structure." Accession No. 1995–109702 [15], Derwent abstract for JP 070 31875, 1995.
Dorschug M. et al., "Mini–pro–insulin contg. A and B chains joined by arginine—useful for treating diabetes and as intermediate for human insulin, and new DNA, fusion proteins, etc." Accession No. 1990–001166 [01], Derwent abstract for EP 0 347 781, Dec. 27, 1989.
Dorshug M. et al., "Mixed crystals for treating diabetes mellitus—consist of two insulin(s), one of which is basically modified on C–terminal end of its b–chain." Accession No.1988–331456 [47], Derwent abstract for EP 0 291 863, Nov. 23, 1988.
Grau U. et al., "Device for applying pharmaceutical suspensions—consists of a container filled with suspension and contg. mixing body of greater density than the suspension." Accession No. 87–243420 [35], Derwent abstract for EP 0 235 691, Sep. 9, 1987.
Grau U., "Prismatic crystalline insulin derivatives production—by cleavage of insulin intermediates, pre–insulin or pre–pro–insulin compounds near isoelectric point in presence of aromatic hydroxy compound." Accession No. 1985–050917 [09], Derwent abstract for EP 0 135 720, Apr. 3, 1985.
Grau U., "Insulin derivs. crystal suspensions production—by crystallisation in aq. medium at isoelectric pt. In presence of aromatic hydroxy cpds." Accession No. 1985–039026 [07], Derwent abstract for EP 0 133 285, Feb. 2, 1985.
Thurow H., "Rhombohedral crystalline insulin strictire transformation—from 4–Zn to 2–Zn form by maintaining in medium contg. less than 6 percent sodium chloride buffered to pH 4.5–6.0." Accession No. 1981–19438B [12], Derwent abstract for EP 0 025 868, Apr. 1, 1981.
Scherer H., "Microcrystalline insulin." Accession No. 1966–01993F [00], Derwent abstract for DE 1 126 561.
Mager A. et al., "Long acting insulin compsns.—contg. a crystalline insulin suspension and des phenyl alanine insuline soln." Accession No. 1975–72486W [44], Derwent abstract for DE 24 18 218, Nov. 13, 1975.
Mager A. et al., "Compsns. contg. amorphous des–Phe (B1)–insulin—have improved storage properties." Accession No. 1974–39935V [22], Derwent abstract for DE 2 256 215, May 30, 1974.
Daopin et al., "Crystal Structure of TGF–β2 Refined at 1.8 Å Resolution," *Proteins: Structure, Function, and Genetics* 17:176–192 (1993).
Graycar et al., "Human Transforming Growth Factor β3. Recombinant Expression, Purification, and Biological Activities in Comparison with Transforming Growth Factors–β1 and –β2," *Molecular Endocrinology* 3(12): 1977–1984 (1989).
Mittl et al., "The crystal structure of TGF–β3 and comparison to TGF–β2: Implications for receptor binding," *Protein Science* 5(7): 1261–1271 (1996).

(List continued on next page.)

Primary Examiner—Christopher S. F. Low
Assistant Examiner—David Lukton
(74) *Attorney, Agent, or Firm*—Hesna J. Pfeiffer

(57) ABSTRACT

The invention concerns TGF-β in a crystalline form which shows no adsorption or less adsorption to the walls of vials than the soluted TGF-β and which is more stable towards oxidative agents than the soluted form. TGF-β crystals of the invention can be used for structure determination and for drug design and for the production of a slow release pharmaceutical preparation.

9 Claims, No Drawings-

OTHER PUBLICATIONS

Schlunegger et al., "An unusual feature revealed by the crystal structure at 2.2 Å resolution of human transforming growth factor–β2, " *Nature* 358: 430–434 (1992).

Schlunegger et al., "Crystallization and preliminary X–ray analysis of recombinant human transforming growth factor β2," *FEBS* 303(1):91–93 (19920).

ten Dijke et al., "Recombinant Transforming Growth Factor Type β3: Biological Activities and Receptor–Binding Properties in Isolated Bone Cells," *Molecular and Cellular Biology* 10(9): 4473–4479 (1990).

Venkataraman et al., "Complex flexibility of the transforming growth factor β superfamily," *Proc. Natl. Acad. Sci. USA* 92:5406–5410 (1995).

* cited by examiner

SEQUENCE LISTING

<160> NUMBER OF SEQ ID NOS: 2

<210> SEQ ID NO 1
<211> LENGTH: 339
<212> TYPE: DNA
<213> ORGANISM: Homo sapiens
<220> FEATURE:
<221> NAME/KEY: CDS
<222> LOCATION: (1)..(336)
<223> OTHER INFORMATION: product = human TGF-beta3

<400> SEQUENCE: 1

```
gct ttg gac acc aat tac tgc ttc cgc aac ttg gag gag aac tgc tgt      48
Ala Leu Asp Thr Asn Tyr Cys Phe Arg Asn Leu Glu Glu Asn Cys Cys
 1               5                  10                  15 gtg cgc ccc ctc tac att gac ttc cga cag gat ctg ggc tgg aag tgg      96
Val Arg Pro Leu Tyr Ile Asp Phe Arg Gln Asp Leu Gly Trp Lys Trp
             20                  25                  30 gtc cat gaa cct aag ggc tac tat gcc aac ttc tgc tca ggc cct tgc     144
Val His Glu Pro Lys Gly Tyr Tyr Ala Asn Phe Cys Ser Gly Pro Cys
         35                  40                  45 cca tac ctc cgc agt gca gac aca acc cac agc acg gtg ctg gga ctg     192
Pro Tyr Leu Arg Ser Ala Asp Thr Thr His Ser Thr Val Leu Gly Leu
     50                  55                  60 tac aac act ctg aac cct gaa gca tct gcc tcg cct tgc tgc gtg ccc     240
Tyr Asn Thr Leu Asn Pro Glu Ala Ser Ala Ser Pro Cys Cys Val Pro
 65                  70                  75                  80 cag gac ctg gag ccc ctg acc atc ctg tac tat gtt ggg agg acc ccc     288
Gln Asp Leu Glu Pro Leu Thr Ile Leu Tyr Tyr Val Gly Arg Thr Pro
                 85                  90                  95 aaa gtg gag cag ctc tcc aac atg gtg gtg aag tct tgt aaa tgt agc     336
Lys Val Glu Gln Leu Ser Asn Met Val Val Lys Ser Cys Lys Cys Ser
            100                 105                 110 tga                                                                  339
```

<210> SEQ ID NO 2
<211> LENGTH: 112
<212> TYPE: PRT
<213> ORGANISM: Homo sapiens

<400> SEQUENCE: 2

```
Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
             20                  25                  30

Val His Glu Pro Lys Gly Tyr Tyr Ala Asn Phe Cys Ser Gly Pro Cys
         35                  40                  45

Pro Tyr Leu Arg Ser Ala Asp Thr Thr His Ser Thr Val Leu Gly Leu
     50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
            100                 105                 110
```

TRANSFORMING GROWTH FACTOR β CRYSTALS

The invention relates to crystals and slow release formulations of Transforming Growth Factor-β (TGF-β).

BACKGROUND OF THE INVENTION

TGF-β plays a central role in many biological regulation pathways such as embryonal development or regeneration of tissue. It is a very potent biological agent which can be used also therapeutically for a series of different purposes.

TGF-β was originally purified to homogeneity from human platelets, human placenta and bovine kidney and identified as a homodimeric protein with a molecular mass of about 25.000 Da. First characterized by its ability to act synergistically with EGF or TGF-α to induce anchorage-independent growth of untransformed NRK cells, recently, TGF-β has been shown to exhibit numerous regulatory effects on a wide variety of both normal and neoplastic cells indicating the importance of this protein as a multifunctional regulator of cellular activity. Depending upon the cell or tissue type, and the presence or absence of other growth factors, TGF-β may either stimulate mitogenesis, cell proliferation and growth, or may effectively inhibit said processes, or may exhibit other actions like e.g. control of adipogenesis, myogenesis, chondrogenesis, osteogenesis and immune cell function, stimulation of chemotaxis, or induction or inhibition of differentiation. Many of the actions of TGF-β are related to the response of cells or tissues to stress or injury, and to the repair of resultant damage. After inflammation, TGF-β plays the major role in the formation of granulation tissue, increases the expression of genes associated with extracellular matrix formation such as fibronectin, collagen and several protease inhibitors and stimulates collagen-matrix contraction by fibroblasts, suggesting its possible role in connective tissue contraction.

The term TGF-β represents a family of functionally and structurally closely related proteins. Until now, five distinct homodimeric TGF-βs designated as TGF-β1, TGF-β2, TGF-β3, TGF-β4 and TGF-β5 are described.

All TGF-βs are synthesized as 390 to 412 amino acid precursors that undergo proteolytic cleavage to produce the mature forms, which consist of the C-terminal 112 amino acids. In their mature, biologically active forms, TGF-β1 to 5 are acid- and heat-stable disulfide-linked homodimers of two polypeptide chains of 112 amino acids each. The complete amino acid sequences of human (Derynck, R. et al. (1985) Nature 316, 701–705), murine (Derynck, R. et al. (1986) J. Biol. Chem. 261, 4377–4379) and simian TGF-β1 (Sharples, K. et al. (1987) DNA 6, 239–244) show remarkable sequence conservation, differing only in a single amino acid residue. Comparison of the amino acid sequence of human TGF-β1, human TGF-β2 (deMartin, R. et al. (1987) EMBO J. 6, 3673–3677; Marquardt, H. et al. (1987) J. Biol. Chem. 262, 12127–12131) and human TGF-β3 (Ten Dijke, P. et al. (1988) PNAS 85, 4715–4719) has demonstrated that the three proteins exhibit in their mature forms about 70–80% sequence identity. A heterodimeric TGF-β1.2 has been isolated from porcine platelets and consists of one subunit of TGF-β1 disulfide-linked to one subunit of TGF-β2 (Cheifetz, S. et al. (1987) Cell 48, 409–415).

Recently, attempts have been undertaken aiming to produce TGF-βs by means of recombinant techniques rather than isolating these factors from natural sources (e.g. platelets) in order to obtain sufficient amounts for testing in various therapeutic modalities. However, it has proven to be extremely difficult to obtain biologically active recombinant TGF-β. As can be seen from the sequences depicted in the sequence listing under SEQ ID NOs.1 to 6, the 112 amino acids long mature forms of TGF-β1, TGF-β2 and TGF-β3 contain 9 cysteine residues. It has been shown for TGF-β2 that the 9 cysteine residues are forming 4 intrachain and 1 interchain disulfide bonds and that it has a complicated core structure ("disulfite knot") [Schlunegger, M. P. and Gruetter, M. G., Nature 358:430–434(1992)]. It is known today that disulfide formation in TGF-β3 is analogous to TGF-β2 and that TGF-β3 exhibits the same complicated core structure.

Although expression of recombinant TGF-βs can be achieved in eukaryotic systems, the yields of biologically active, correctly folded material obtained are still far from being satisfactory. Therefore, attempts were made to produce biologically active TGF-β in a microbial host. However, in e.g. bacteria the intracellular conditions are not conducive to correct folding, disulfide bond formation and disulfide-stabilized dimerization which is apparently essential for activity. Thus, only very little biologically active TGF-β could be obtained after expression of the respective gene in *E. coli* under the control of the lambda promoter as described in European Patent Application EP-A-0 268 561. Another report describes the expression of a TGF-β cDNA in *E. coli* under the control of the trp promoter yielding a radioactively labelled protein band with an apparent molecular weight of 13'000 Da in an autoradiogram of a SDS polyacrylamide gel, but no activity was measured (Urushizaki, Y. et al. (1987) Tumor Res. 22, 41–55). However, in e.g. the European patent application EP-A-0 433 225 a successful process for the production of biologically active, dimeric TGF-β-like protein is described, in which a mild detergent is used for the folding of TGF-β isolated from inclusion bodies.

However, in preparing a pharmaceutically acceptable formulation the problem arises that TGF-β3 tends to absorb unspecificaly to several materials and is therefore difficult to administer in exact quantities. Moreover, like all proteins, TGF-β3 is sensitive towards oxidative agents such as oxygen in air.

It was found in the present invention that the use of TGF-β3 crystals instead of the soluted form prevents both against instability and adsorption.

In Schlunegger at al., FEBS Lett.303:91–93(1992) crystallization of TGF-β2 is described by the hanging drop method described in Schär et al., J. Biol. Chem. 262:13724 (1987) from a 25–35% polyethylene glycol 400 solution. Likewise, in U.S. Pat. No. 5,322,933 TGF-β1 and TGF-β2 crystals were prepared by the hanging drop method using 20% PEG 200 and 600, respectively.

OBJECT OF THE INVENTION

It is an object of the invention to provide TGF-β3 in a crystalline form in order to provide a form which shows no adsorption or less adsorption to the wall of vials than the soluted TGF-β3. It is further an object of the invention to provide TGF-β in crystalline form in order to provide a form which is more stable towards oxidative agents than the soluted form.

Another object of the invention is to provide TGF-β3 crystals which can be used for structure determination and for drug design.

A further object of the invention is to provide a pharmaceutical preparation of TGF-β which contains TGF-β crystals and can be used as or for the production of a slow release pharmaceutical preparation.

SUMMARY OF THE INVENTION

Surprisingly, it was found that TGF-β3 forms crystals which are stable in aqueous solutions. TGF-β3 crystals do not stick to the walls of the glass vessel and the protein is protected against degradation, and which can be used for structure determination and for drug design.

Moreover, it was surprisingly found that TGF-β crystals can be used as or for the preparation of slow release formulations for therapeutic applications of TGF-β. If crystalline TGFβ is applied to the patient, the concentration of soluble and, thus, available TGF-β can be varied by selecting crystals with different solution properties or by the appropriate crystal size.

DETAILED DESCRIPTION OF THE INVENTION

The present invention concerns crystals of TGF-β3, preferably TGF-β3 crystals selected from the group consisting of crystals belonging to a hexagonal or trigonal space group, more preferably crystals selected from the group consisting of crystals belonging to the hexagonal space group $P6_122$ or to the trigonal space group $P3_221$, even more preferably hexagonal crystal form "H" belonging to hexagonal space group $P6_122$ with unit-cell dimensions of a=b=77.8 Å, c=143.2 Å, α=β=90°, γ=120° (depending on the exact crystallization conditions, the unit-cell dimensions of this preferred form can vary up to 4%), even more preferably trigonal crystal form "T" belonging to the trigonal space group $P3_221$ with unit-cell dimensions of a=b=49.3 Å, c=78.9 Å, α=β=90°, γ=120°. Of the hexagonal crystals those are preferred which diffract X-rays to a higher maximal resolution than 4 Å.

The invention also concerns a composition consisting essentially of crystals of TGF-β3, preferably TGF-β3 crystals selected from the group consisting of crystals belonging t0 a hexagonal or trigonal space group, more preferably crystals selected from the group consisting of crystals belonging to the hexagonal space group $P6_122$ or to the trigonal space group $P3_221$, even more preferably hexagonal crystal form "H" belonging to hexagonal space group $P6_122$ with unit-cell dimensions of a=b=77.8 Å, c=143.2 Å, α=β=90°, γ=120° (depending on the exact crystallization conditions, the unit-cell dimensions of this preferred form can vary up to 4%), even more preferably trigonal crystal form "T" belonging to the trigonal space group $P3_221$ with unit-cell dimensions of a=b=49.3 Å, c=78.9 Å, α=β=90°, γ=120°.

The invention further concerns a pharmaceutical composition comprising crystals of TGF-β3, preferably TGF-β3 crystals selected from the group consisting of crystals belonging to a hexagonal or trigonal space group, more preferably crystals selected from the group consisting of crystals belonging to the hexagonal space group $P6_122$ or to the trigonal space group $P3_221$, even more preferably hexagonal crystal form "H" belonging to hexagonal space group $P6_122$ with unit-cell dimensions of a=b=77.8 Å, c=143.2 Å, α=β=90°, γ=120° (depending on the exact crystallization conditions, the unit-cell dimensions of this preferred form can vary up to 4%), even more preferably trigonal crystal form "T" belonging to the trigonal space group $P3_221$ with unit-cell dimensions of a=b=49.3 Å, c=78.9 Å, α=β=90°, γ=120°.

Normally protein crystals are held together by the interaction of charged groups and dipoles on the surface between symmetry related molecules. The high resolution X-ray structure analysis of TGF-β3 revealed that this is not the case for the form T crystals. These crystals are very densely packed, but only very few polar interactions are involved in crystal contacts. Most of these contacts are mediated by hydrophobic interactions. This unusual construction causes a surprisingly high stability of the crystal form T in contrast to many other protein crystals which are relatively fragile and tend to dissolve easily under physiological conditions: Crystals of form T are mechanically stable. They can be manipulated by hand without cracking. In the reservoir buffer they are durable for at least 6 month. The crystals are also stable under physiological conditions, e.g. in a PBS-buffer (125 mM NaCl, 5 mM KCl, 5 mM $MgCl_2$, 25 mM $Na_2HPO_4$, pH 7.2). The crystals dissolve in 100 mM acetic acid or in the presence of isopropanol.

Crystals of form H are relatively fragile and crack easily if they are toughed with a needle. If they are transfered to solutions different from the mother liquor, they get rents immediately.

Moreover, the invention concerns a method for the preparation of the crystals.

Pure dimeric, biologically active TGF-β3 from any source can be used as starting material for crystallization, for example such isolated from a natural source, produced in recombinant eukaryotic expression systems such as CHO cells, or produced in prokaryotic expression systems such as *E. coli*. For example, TGF-β3 expressed as inclusion bodies in *E. coli*, solubilized, refolded, for example by a method using the mild detergent CHAPS and, optionally, the organic solvent DMSO, and purified, for example by suitable chromatography procedures such as cation exchange chromatography or HPLC, can be used as staring material.

In the crystallization process a crystallization buffer is prepared (e.g. by mixing a TGF-β3 solution with a "reservoir buffer") with a lower concentration of a precipitating agent than necessary for crystal formation. For crystal formation, the concentration of the precipitating agent has to be increased, e.g. by addition of precipitating agent, for example by titration, or by allowing the concentration of precipitating agent to change by diffusion between the crystallization buffer and a reservoir buffer, for example diffusion of the precipitating agent from a reservoir buffer having a higher concentration of precipitating agent into the crystallization buffer. For example, diffusion can be achieved by vapour diffusion techniques—in such methods the conditions in the crystallization buffer are changed by diffusion in the common gas phase—such as the "hanging drop" or "sitting drop" method, in which a drop of crystallization buffer is hanging above or sitting beside, respectively, a much larger reservoir of the reservoir buffer, or a vapour diffusion batch method e.g. as described in the examples. The change of the concentration of precipitating agent can also be achieved, for example, by diffusion of the precipitating agent through a semipermeable membrane that separates the crystallization buffer from the reservoir buffer and prevents the penetration of the protein into the reservoir buffer.

TGF-β3 in the crystallization buffer preferably has a concentration of up to 10 mg/ml, more preferably 0.5 to 6 mg/ml, even more preferably 1 to 3 mg/ml.

The preparation of TGF-β3 crystals can be performed under various conditions. The preferred pH is from pH 4 to 8.5. Since the concentration and type of buffer is not important, a variety of buffers can be used. Preferred buffer systems are potassium phosphate, sodium citrate, sodium acetate, Tris or HEPES The buffer contains a precipitating agent which is selected from the group consisting of a water miscible organic solvent, preferably with a low relative dielectric constant, such as isopropanol, acetonitril, DMSO, or, preferably, dioxane, and polyethylene glycol, preferably such having a molecular weight of between 400 and 8000.

Trigonal crystals of TGF-β3 are obtained under several conditions. The preferred pH is from pH 4 to 7.5. Preferred buffer systems for obtaining T crystals are Tris, and, more preferred, potassium phosphate, sodium citrate, sodium acetate, or HEPES. In a preferred embodiment of the invention the crystallization buffer comprises between 30 mM and 300 mM of the buffer substance, more preferably 50 to 150 mM of the buffer substance. Trigonal TGF-β3 crystals are formed in the presence of a water miscible organic solvent as the precipitating agent, preferably with a low relative dielectric constant, such as isopropanol, acetonitril, DMSO, or, preferably, dioxane, the organic solvent being present in a concentration of 6 to 30%, preferably 6 to 15%. The temperature is preferably between 4° C. and 20° C.

For obtaining TGF-β3 crystals of form T, the preferred dioxane concentration in the crystallization buffer is 7.5%. As already defined above, the crystal form T thus obtainable belongs to the trigonal space group $P3_221$ with unit-cell dimensions of a=b=49.3 Å, c=78.9 Å, $\alpha=\beta=90°$, $\gamma=120°$.

Hexagonal crystals of TGF-β3 grow under several conditions. The preferred pH is from pH 5.0 to pH 8.5. Preferably polyethylenglycols with a molecular weight from 400 to 8000 and a concentration from 10% to 30% are present in the crystallization buffer. The preferred temperature is between 4° C. and 20° C. The crystals grow as hexagonal bipyramids.

TGF-β3 crystals of the present invention can be formed either in batch crystallization or with the hanging drop method well known in the art for the crystallization of proteins. Examples of both methods are detailed hereinafter.

TGF-β3 crystals of the present invention can either be prepared by spontaneous crystallization or, more advantageously, by micro seeding or macro seeding as described hereinafter in the examples. Especially the use of a micro crystalline suspension for seeding ("micro seeding") provides a good method to control the crystal size. For example, in the case of T crystals, dilutions of $1/4^3$ to $1/4^5$ of a stock suspension containing 0.1 mm³ homogenized TGF-β3 crystals per 100 μl suspension yield crystals with a typical size around 10×10×30 μm³. At higher ($1/4^6$ to $1/4^9$) single, large crystals grow (size 70×70×250 μm³). The lower the crystal size the larger the surface of the crystals in a formulation comprising a given amount of TGF-β3. Thus, crystal surface has an influence on the amount of soluted TGF-β3 in equilibrium with the crystals, and thus on the amount of the available TGF-β3 in the slow release formulation.

The application of TGF-β3 as a suspension of crystals, preferentially of form T, has some advantages over the application in solution. For example, in the crystalline state, preferentially in form H and more preferably in form T, unspecifc absorption to the vessel surfaces and protein degradation is diminished. Another advantage is that TGF-β3 crystals, preferably form H and more preferably form T, can be used as or for the production of a slow release formulation for therapeutic application.

TGF-β3 crystals, preferentially form T, are also stable under physiological conditions therefore can be used as or for the production of a slow release formulation.

Another aspect of the present invention concerns slow release formulations comprising TGF-β crystals. In a preferred embodiment of the invention, "TGF-β" in context with slow release formulations hereinafter means a TGF-β selected from the group consisting of TGF-β1, TGF-β2, TGF-β3, TGF-β4 and TGF-β5, more preferably TGF-β1, TGF-β2 and TGF-β2, and TGF-β3, even more preferably TGF-β3.

Crystals of TGF-β1 and TGF-β2 can be prepared according to methods already known in the art, e.g. as described in Davies et al., U.S. Pat. No. 5,322,933.

Crystals of TGF-β are suitable as or for the production of a slow release formulation due to the depot effect of the crystals. Preferred are formulations with which concetrations of available TGF-β of 0.1 to 50 μg/ml can be achieved.

Depot crystal formulations of TGF-β can be in the form of gels, ointments, suspensions. The crystals can be mixed with all acceptable pharmaceutical ingredients such as cellulose derivatives, sugars, polymers, salts, preservatives. The TGF-β crystals can be used also in the preparation of lyophilized formulations and included e.g. in dry dressings and bone cements. Depot formulations of TGF-β can be used in all TGF therapeutical areas, e.g. in wound healing, oral mucositis, osteoarthritis, bone diseases, bone repair, or intestinal mucositis.

Another aspect of the invention is the use of the TGF-β3 crystals of the present invention for structure determination and for drug design.

For the rational design of drugs the three-dimensional structure of the target protein has to be known. At the moment this structural information can only be achieved either spectroscopically in solution by NMR, by X-ray diffraction at protein crystals or by homology modeling. Structural information achieved by modeling based on a homolous structure is not sufficiently detailed and structures that are supported by experimental evidence are therefore preferred. Crystals that are useful to support the rational design of drugs have to possess different properties. First of all the structure has to be of high resolution in order to yield a detailed description of the molecule. The highest reachable resolution depends on the quality of the protein crystals. Furthermore small molecules must be able to penetrate the crystal in order to reach the active site. If this active site is blocked by other compounds, such as neighboring molecules, inhibitors or any substance that is required for crystallization, a different crystal form has to be used.

Crystal form "T" yield a higher resolution than crystal form "H" and is therefore preferred for drug design. Due to the dense packing of crystal form "T" a large fraction of the molecular surface is not accessible for drugs. In cases where due to this reason the drug does not bind to TGF-β3 in crystal form "T", crystal form "H" is preferred over crystal form "T".

The following examples illustrate the invention without being meant to be limitative.

EXAMPLE 1

Expression of TGF-β1, TGF-β2 and TGF-β3 in *E. coli*

EXAMPLE 1A

General Methods

Bacterial Strain

*E. coli* K12/LC 137: htpR$_{am}$, lon$_{R9}$, lac$_{am}$, mal$_{am}$, trp$_{am}$, pho$_{am}$, rspL, tsx::Tn10, supC$_{ts}$ (Goff, S. A. et al. (1984) PNAS 81, 6647–6651).

Plasmids pPLMu (Buell, G. et al. (1985) Nucleic Acids Res. 13,1923–1938): This plasmid carries the bacteriophage I $P_L$ promoter with the phage Mu ner gene ribosome binding site (Van Leerdam, E. et al. (1982) Virology 123, 19–28).

$pcl_{857}$: Plasmid encoding a thermolabile $\lambda cl_{857}$ repressor and conferring resistance to kanamycin (Remault, E. et al. (1983) Gene 22, 103–113).

SDS Gel-electrophoresis

SDS polyacrylamide gel-electrophoresis (SDS-PAGE) and protein staining is done as described previously (Laemmli, U. K. (1970) Nature 227, 680–685) using the Miniprotean II cell from BIORAD and 1 mm thick 18% polyacrylamide gels.

Heat Induction 7 ml of LB-Medium (Maniatis et al. (1982), Molecular Cloning, Cold Spring Harbor Laboratory, New York) in a 20 ml culture tube containing 40 µg of each ampicillin and kanamycin (LB/amp/kan) are inoculated with a single colony and incubated with shaking overnight at 30° C. 5 ml of this overnight culture are added to 15 ml of LB/amp/kan in a 100 ml Erlenmeyer flask. This flask is transferred to a 42° C. waterbath shaker. A 2 ml sample is taken before transfer (non-inducing conditions) and 1 ml samples at 1 hour intervals after the transfer (inducing conditions). Cells are pelleted by centrifugation (5 min, 10.000 rpm in an Eppendorf centrifuge) and the supernatant is discarded. The pellet is resuspended in 100 µl of sample buffer for SDS-PAGE and heated for 10 min at 95° C. 5 µl aliquots are loaded for SDS-PAGE.

Preparation of Competent Cells

Competent E. coli cells are prepared by the calcium chloride procedure as described in Maniatis et al. (1982), Molecular Cloning, Cold Spring Harbor Laboratory, New York. Cells carrying plasmid $pcl_{857}$ are grown at 30° C.

EXAMPLE 1B

Construction of Expression Vector pPLMu.hTGF-β3 and expression of TGF-β3

The coding sequence of TGF-β3 (shown in the sequence listing under SEQ ID No. 1) is cloned into plasmid PGem-5ZF(+) (Promega) digested with NcoI, dephosphorylated with Calf Intestinal Alkaline Phosphatase (Boehringer) and filled in with Klenow polymerase (Gibco-BRL). The resulting construct is designated as pGKM 126 and is used to transform competent E. coli Y 1090 cells. Clones carrying the correct insert encoding TGF-β3 is designated as E. coli Y1090/pGKM 126.

E. coli Y1090/pGKM 126 cells are grown in LB medium and plasmid DNA is prepared by the method of Birnboim, H. C. and Doly, H. (1979) Nucleic Acids Research 7, 1513. 5 µg of plasmid DNA are cut to completion in 50 µl restriction buffer with NcoI following the recommendations of the supplier (Boehringer). The DNA is precipitated by addition of 5 µl 3 M sodium acetate, 100 mM $MgCl_2$, 5 mM EDTA and 150 µl ethanol. After incubation at −70° C. for 15 min the DNA is pelleted by centrifugation at 13.000 g for 15 min in a SS34 rotor in a Sorvall centrifuge. The supernatant is discarded and the pellet is resuspended in 80 µl 0.089 M TRIS borate, 0.089 M boric acid and 0.002 M EDTA (TBE buffer) containing 0.25% bromphenol blue and 0.25% xylene cyanol. 4 times 20 µl samples are electrophoresed through a 1% agarose gel in TBE buffer containing 0.5 µg/ml ethidium bromide at 50 volts till the bromphenol blue marker reaches the bottom of the 10 cm long and 0.8 cm thick gel. The DNA fragment coding for mature TGF-β3 is visualized under short wave UV light, cut out with a razor blade and electroeluted from the gel piece in a Schleicher & Schüll Biotrap apparatus applying 200 mamp for 1.5 hours. The eluted DNA fragment is precipitated (see above) and resuspended in 20 µl TE.

5 µl of plasmid pPLMu are linearized by digestion with either NcoI and SalI, NcoI and EcoRV or NcoI alone and gel purified as described above for the fragment DNAs. 100 ng of the linearized and purified pPLMu vector DNA and 3 times the molar equivalent of the respective purified fragment DNA are incubated at 4° C. for 15 hours in 20 µl of ligation buffer (70 mM TRIS/HCl, pH 7.5, 10 mM $MgCl_2$, 5 mM DTT, 0.1 mM adenosine-triphosphate) containing 1 unit of DNA ligase (Boehringer).

10 µl of the ligation mixture are added to 200 µl of cold (4° C.) competent E. coli LC 137 cells carrying plasmid $pcl_{857}$ After 30 min the cells are heat shocked by incubation for 1.5 min in a 42° C. water bath. 2 ml of LB medium are added and the culture is shaken for 60 min at 30° C. 200 µl aliquots are plated on LB plates containing ampicillin and kanamycin and incubated for 22 hours at 30° C. Single colonies are cultivated and plasmid DNA is analysed. Subcloning of the DNA fragment coding for TGF-β3 in pPLMu results in plasmids pPLMu.hTGF-β3. Clones containing the above construct are referred to as E. coli LC 137/pPLMu.hTGF-β3.

E. coli LC 137/pPLMu.hTGF-β3 cells are heat induced (see example 1A) and the expressed protein is analysed by SDS-PAGE. TGF-β3 all appear 2 hours after heat induction as heat induced proteins migrating with an apparent molecular mass of approximately 12.000 Da.

EXAMPLE 1C

Fermentation of Transformants

Overnight cultures of E. coli LC137/pPLMu.h.TGF-β3 in 2 l Erlenmeyer flasks containing 750 ml of LB medium with 40 mg/l of ampicillin and kanamycin are grown at 30° C. 300 ml of the overnight cultures are added to 750 ml of LB medium containing antibiotics as mentioned above in 2 l Erlenmeyer flasks and heated to 42° C. by shaking for approximately 3.5 minutes in a 65° C. water bath. The flasks are then transferred to a 42° C. shaker and incubated for 3 hours. The flasks are cooled down to 12° C. in an ice water bath and the cells are collected after centrifugation for 10 minutes at 8.000 rpm in a GSA rotor (Sorvall).

EXAMPLE 2

Example 2A

Recovery of Non-soluble, Monomeric TGF-β3 from E. coli

E. coli LC 137/pPLMu.hTGF-β3 cells are fermented as described in Example 1C. Cell disruption and recovery of non-soluble TGF-β3 is performed at 4° C. About 18 g of wet cells are suspended in 60 ml of 0.1 M TRIS/HCl, 10 mM EDTA, 1 mM PMSF (Phenyl Methan Sulphonyl Fluoride), pH 8.3 (disruption buffer). The cells are passed two times through a Frenchpress (SLM Instruments, Inc.) according to the manufacturers instructions and the volume is brought to 200 ml with the disruption buffer. The suspension is centrifuged for 20 min at 15.000 g. The pellet obtained is suspended in 100 ml disruption buffer containing 1 M NaCl and centrifuged for 10 min as above. The pellet is suspended in 100 ml disruption buffer containing 1% Triton X-100

(Pierce) and again centrifuged for 10 min as above. The washed pellet is then suspended in 50 ml of 20 mM Tris/HCl, 1 mM EDTA, 1 mM PMSF, 1% DTT and homogenised in a Teflon tissue grinder. The resulting suspension contains crude monomeric TGF-β3 in a non-soluble form.

EXAMPLE 2B

Solubilization and Purification of Monomeric TGF-β3

10 ml of the TGF-β3 suspension obtained according to Example 2A are acidified with 10% acetic acid to pH 2.5 and centrifuged in an Eppendorf centrifuge for 10 min at room temperature. The supernatant is chromatographed on a Sephacryl S-100 column (Pharmacia, 2.6×78 cm) in 10% acetic acid at a flow rate of 1.4 ml/min. (Alternatively, the chromatography can be performed on Sephacryl S-100HR (Pharmacia) and the column can be run in 1% acetic acid or 5 mM HCl, respectively.) Fractions containing monomeric, denatured TGF-β3 eluting between 190 min and 220 min are pooled. This material is used for folding to get biologically active, dimeric TGF-β3.

EXAMPLE 3

In Vitro Folding of TGF-β3

TGF-β3 obtained above is folded at 4° C. in a buffer consisting of 0.1 M Tris, 30 mM CHAPS, 1 M NaCl, 5 mM reduced glutathione and 20% (v/v) DMSO respectively. If necessary the pH of the buffer is adjusted to pH 9.5 with NaOH. The final concentration of TGF-β3 is 0.1 mg/ml. After 7 days at 4° C. the solution is acidified with concentrated acetic acid to pH 3.5, concentrated about 10 times by ultrafiltration in an Amicon stirred cell with YM10 membrane (Amicon). The concentrated solution is diluted to the original volume with 0.1 M acetic acid and reconcentrated. This procedure is repeated 2 times. The solution is then subjected to purification steps as described in Example 4.

EXAMPLE 4

Purification of Dimeric Biologically Active TGF-β3

The solution obtained in Example 3 containing between about 10 and 50 mg TGF-β3 is subjected to a diafiltration step using 50 mM acetic acid, 35% ethanol. The resulting solution is loaded at 6 ml/min onto a HiLoad 26/10 S-Sepharose High Performance column (Pharmacia). The column is first washed with 50 mM acetatic acid, 35% ethanol (buffer A) for 5 minutes and then eluted with a linear gradient over 45 min starting with buffer A containing 0.2 M NaCl and ending with buffer A containing 0.5 M NaCl. The eluate is monitored at 280 nm and fractionated manually. Fractions are checked for dimeric TGF-β3 by non-reducing SDS-PAGE and for biological activity by in vitro bioassay according to example 5.

Fractions containing dimeric biologically active TGF-β3 are pooled, dialysed against 0.1 M acetic acid or diluted with the same volume of 0.1% TFA in water and subjected to RP-HPLC on a Vydac 214TP510 column (1 cm×25 cm, The Separations Group, USA). The column is equilibrated at a flow rate of 4.5 m/min with a mixture of 75% solvent A [TFA 0.1% in water] and 25% solvent B [TFA 0.08% in acetonitrile]. After loading of the sample the column is washed under equilibration conditions until the absorption monitored at 235 nm has reached baseline level. The column is then eluted within 30 min with a linear gradient starting at equilibration conditions and ending with a mixture of 45% solvent A and 55% solvent B. The eluate is fractionated manually and analyzed by non-reducing SDS-PAGE and by in vitro bioassay according to Example 5.

Active fractions are pooled and diafiltrated against 20 mM acetic acid, 20% ethanol.

EXAMPLE 5

In vitro Activity Test for Folded TGF-β: Mink Lung Epithelial Cell (Mv-1-Lu) Acid Phosphatase Assay TGF-β3 is screened in vitro, in a cellular bioassay which measures the potency of the compound in inhibiting the growth of a continuous mink lung epithelial cell line Mv-1-Lu (ATCC/CCL64). The Mv-1-Lu cell line has proven to be a sensitive reporter in the bioassay for TGF-β, exhibiting a sigmoid-shaped concentration response with a reported EC50 of approximately 10–50pg/ml (Tucker et al., Science 1984; 226: 705–707; Absher et al., J Immunol Methods 1991; 138: 301–303; Danielpour et al., J Cell Physiol 1989; 138: 79–86). Mv-1-Lu cells, whose proliferation is strongly inhibited by TGF-β, is currently considered as the cell line most suitable for the development of an analytical bioassay for this cytokine (Kelley et al., Exp Lung Res 1992; 18: 877–887; Meager, J Immunol Methods 1991; 141: 1–14). The assay is performed in 96-well microtitre plates using cells which were originally obtained, at passage 46, from the American Type Culture Collection, Rockville Md., USA.

The cells are seeded at low density (5000 cells per well) in growth medium (Minimum Essential Medium with 5% v/v Foetal Calf Serum) containing serial dilutions of a TGF-β3 standard or sample. Assays are then incubated at 37° C. in a humidified 5% $CO_2$ incubator for 72 hrs. Inhibition of cell proliferation is determined by a sensitive enzymatic cell staining method (which gives a colorimetrical estimate of the amount of acid phosphatase produced in each well), the intensity of staining corresponding to the number of cells present in each well. The absorbance O.D. of each well is determined at 405 nm and the assay data is plotted and analysed by means of a suitable PC software programme.

EXAMPLE 6

Crystal Form T (Trigonal)

Dimeric TGF-β3 obtained in Example 4 is dialyzed (membrane Spectrapore MwCO 6–8 kDa) against 10 mM acetic acid in the cold (4° C.) for 17 hours. The TGF-β3 solution is concentrated by ultrafiltration to a final protein concentration of 3–8 mg/ml.

EXAMPLE 6A

Spontaneous Crystallization

2 μl of the TGF-β3 solution in 10 mM acetic acid is mixed with 2 μl reservoir buffer (15% (v/v) dioxane and 100 mM sodium acetate, pH 5.0) on a siliconized cover slip. The cover slip is inverted and placed over a reservoir vessel that is filled with 600 μl reservoir buffer. Reservoir vessel and cover slip are sealed with silicon oil ("hanging drop method"). The chamber volume of the sealed vessel is 2 ml. The distance between drop and reservoir is 12 mm. After 24 hours at room temperature the first crystals (size 10×10×30 μm$^3$) are discovered under the light microscope. The crystals reach their maximum sizes (70×70×250 μm$^3$) after approximately one week. The reproducibility of the crystallization under these conditions is as follows: In 24 of 48 identical crystallization experiments crystals are formed.

EXAMPLE 6B

Microseeding

In order to improve the crystallizability the protein solution can be seeded with crystals obtained by spontaneous crystallization in Example 8A.

One seed crystal (size 30×30×100 μm³) is washed with 10 mM acetic acid and homogenized in 100 μl 10 mM acetic acid. 25 μl of this solution is diluted with 75 μl of 10 mM acetic acid (total dilution 1/4¹). The dilution is repeated 8 times (total dilution 1/4⁸). 1 μl of each dilution is added to the droplet (see above in Example 8A) before the reservoir vessel is sealed with the cover slip. The size and the number of crystals produced per drop depends on the dilution of the micro crystal suspension. With undiluted suspensions a micro crystalline precipitate is discovered (for the purpose of the present invention, micro crystal is defined as having a size in the longest dimension of less than 3 μm). Dilutions of 1/4³ to 1/4⁵ yield microcrystals with a typical size around 10×10×30 μm³. At higher dilutions (1/4⁶ to 1/4⁹) single, large crystals grow (size 70×70×250 μm³). Thus, the use of microcrystalline suspensions for seeding provides a good method to control the crystal size.

EXAMPLE 6C

Further Crystallization Conditions

Crystals are obtained by spontaneaous crystallization, micro- or macro-seeding using conditions summarized in the following table:

| buffer | precipitating agent | reservoir buffer: protein solution [μl] |
|---|---|---|
| 100 mM K-PO4, pH 6.0 | 6% dioxane | 2:2 |
| " | 9% dioxane | " |
| " | 15% dioxane | " |
| 100 mM Na-citrat, pH 4.0 | 15% dioxane | 2:2 |
| 100 mM Na-citrat, pH 4.5 | " | " |
| 100 mM NaOAcetate, pH 5.0 | " | " |
| 100 mM NaOAcetate, pH 5.5 | " | " |
| 100 mM K-PO4, pH 6.5 | " | " |
| 100 mM K-PO4, pH 7.0 | " | " |
| 100 mM HEPES, pH 7.5 | " | " |
| 30 mM NaOAcetate, pH 5.0 | " | 2:2 |
| " | " | 3:1 |
| 100 mM NaOAcetate, pH 5.0 | " | 3:1 |
| 300 mM NaOAcetate, pH 5.0 | " | 2:2 |
| " | " | 3:1 |

EXAMPLE 6D

Macroseeding

Single macro crystals can be used for seeding instead of the micro crystaline suspension. (for the purpose of the present invention, macro crystal is defined as having a size in the longest dimension of 3 μm or more) The seed crystal (size 30×30×100 μm³) is washed with 10 mM acetic acid for 15 minutes and transferred directly into the droplet (see above in Example 8A). New crystals form within 24 hours and reach a size around 50×50×150 μ³.

EXAMPLE 6E

Crystallization by Dialysis

12 μl of TGF-β3 solution in 10 mM acetic acid is mixed with 12 μl reservoir buffer (15% (v/v) dioxane and 100 mM sodium acetate, pH 5.0) and 1 μl of a 1/4⁵ dilution of micro crystal suspension in 10 mM acetic acid (see Example 6B). The mixture is dialysed in the cold (4° C., membrane Spectrapore MwCO 6–8 kDa) against 50 ml of reservoir solution in a sealed beaker.

EXAMPLE 6F

Characterization of the Crystals

Crystal form T belongs to the trigonal space group P3₂21 with unit-cell dimensions of a=b=49.3 Å, c=78.9 Å, α=β90°, γ=120°. The crystals show a rod-like shape with an hexagonal intersection. The crystals such obtained diffract X-ray to a maximum resolution of 2 Å.

Crystals of form T are mechanical stable. They can be manipulated by hand without cracking. In the reservoir buffer they are durable for at least 6 month. The crystals are also stable under physiological conditions. In a PBS-buffer (125 mM NaCl, 5 mM KCl, 5 mM MgCl₂, 25 mM Na₂HPO₄, pH 7.2) the crystals do not dissolve within one week, as judged by visual inspection. The crystals dissolve in 100 mM acetic acid or in the presence of isopropanol.

TGF-β3 T crystals obtained above contain one dioxane molecule per TGF-β3 subunit buried between two symmetry related TGF-β3 molecules.

EXAMPLE 6G

Scale-up

In order to scale-up the crystallization process from 20 μg to 1 g of TGF-β3, the experimental set-up is switched from the hanging drop method to batch crystallization. A batch crystallization experiment is performed as follows: A glass beaker is filled with 200 ml of 5 mg/ml TGF-β3, 7.5% (v/v) dioxane, 50 mM sodium acetate (pH 5.0) and 1 ml of a microcrystal suspension in 10 mM acetic acid. This beaker is placed into a 4 l tank that is filled with 2 l of reservoir buffer (100 mM sodium acetate, pH 5.0, 15% (v/v) dioxane). During crystallization, the reservoir buffer is slightly stirred. After sealing the tank the equilibration between the solution in the beaker and the reservoir across the gaseous phase takes place.

EXAMPLE 7

Crystal Form H (Hexagonal)

As above, dimeric TGF-β3 solution obtained in Example 4 is dialyzed (membrane Spectrapore MwCO 6–8 kDa) against 10 mM acetic acid in the cold (4° C.) for 17 hours. The TGF-β3 solution is concentrated by ultrafiltration to a final protein concentration of 3–8 mg/ml.

EXAMPLE 7A

Crystallization

The crystals of form H are grown using the same "hanging drop" experimental set-up like for the crystal form T. The reservoir buffer consists of 30% (v/v) polyethylenglycol (PEG) 400 and 100 mM potassium phosphate, pH 6.0. 4 μl of the TGF-β3 solution is mixed with 2 μl reservoir buffer. Crystals grow spontaneously within 48 hours at room temperature and reach a size of 400×400×300 μm³.

EXAMPLE 7C

Further Crystallization Conditions

Crystals of form H are obtained by spontaneaous crystallization, micro- or macro-seeding using conditions summarized in the following table:

| buffer | precipitating agent | reservoir buffer; protein solution [μl] |
|---|---|---|
| 100 mM NaOAc, pH 5.0 | 30% PEG550 | 3:1 |
| 100 mM K-PO4, pH 5.5 | " | " |
| 100 mM K-PO4, pH 6.0 | 30% PEG400 | " |

-continued

| buffer | precipitating agent | reservoir buffer; protein solution [μl] |
|---|---|---|
| " | 30% PEG550 | " |
| " | 30% PEG1000 | " |
| 100 mM K-PO4, pH 6.5 | 30% PEG400 | " |
| " | 30% PEG550 | " |
| " | 30% PEG1000 | " |
| " | 30% PEG2000 | " |
| " | 30% PEG3350 | " |
| " | 30% PEG6000 | " |
| " | 30% PEG8000 | " |
| 100 mM K-PO4, pH 7.0 | 30% PEG400 | " |
| " | 30% PEG550 | " |
| " | 30% PEG1000 | " |
| " | 30% PEG2000 | " |
| " | 30% PEG3350 | " |
| " | 30% PEG6000 | " |
| " | 30% PEG8000 | " |
| 100 mM HEPES, pH 7.5 | 30% PEG1000 | " |
| 100 mM Tris/HCl, pH 8.0 | 30% PEG4000 | " |
| 100 mM Tris/HCl, pH 8.5 | " | " |
| 100 mM K-PO4, pH 6.0 | 20% PEG400 | " |
| " | " | 2:1 |
| " | 30% PEG400 | " |

EXAMPLE 7D

Characterization

Crystal form H belongs to the hexagonal space group P6$_1$22 with unit-cell dimensions of a=b=77.8 Å, c=143.2 Å, α=β=90°, γ=120°. Depending on the exact crystallization conditions, the unit-cell dimensions can vary up to 4%. The crystals grow as hexagonal bipyramids. The crystals such obtained diffract X-ray to a maximum resolution of 3.3 Å.

Crystals of form H are relatively fragile and crack easily if they are toughed with a needle. If they are transfered to solutions different from the mother liquor, they get rents immediately.

EXAMPLE 8

Slow Release Properties of TGF-β3 Crystals T and H 2 ml of a suspension of T form TGF-β3 micro crystals (1 mg/ml) are centrifuged for 2 min. in an Eppendorf centrifuge (×1000 rpm). The clear supernatant (S0) is removed and the amount of TGF-β3 is measured. Over the pellet of T micro crystals 2 ml of water are added and the crystals are re-suspended by gentle shaking. After 1 hour equilibration time the solution containing the re-solubilised TGF crystals is centrifuged again (conditions previously described). The amount of TGF-β3 in the supernatant obtained after this first re-solubilisation step (S1) is measured. The pellet of TGF-β3 micro crystals is again suspended in 2 ml of water, incubated for 1 hour and then centrifuged again; the amount of TGF-β3 in the supernatant S2 is measured. The experiment shows that TGF-β3 is present in S1, S2, S3 proving the slow released properties of the T micro crystals.

2 ml of a suspension of H form TGF-β3 micro crystals (1 mg/ml) are centrifuged for 2 min. in an Eppendorf centrifuge (×1000 rpm). The clear supernatant (S0) is removed and the amount of TGF-β3 is measured. Over the pellet of H micro crystals 2 ml of water are added and the micro crystals are re-suspended by gentle shaking. After 1 hour equilibration time the solution containing the re-solubilised TGF-β3 micro crystals is centrifuged again (conditions previously described). The amount of TGF-β3 in the supernatant obtained after this first re-solubilisation step (S1) is measured. The pellet of TGF-β3 micro crystals is again suspended in 2 ml of water, incubated for 1 hour and then centrifuged again; the amount of TGF-β3 in the supernatant S2 is measured. The experiment shows that TGF-β3 is present in S1, S2, S3 proving the slow released properties of the H micro crystals. However, compared with T micro crystals above, the experiments performed with H TGF-β3 micro crystals show a faster solubilization.

EXAMPLE 9

Chemical Stability of TGF-β3 Crytals T and H 2 ml of a suspension of T form TGF-β3 micro crystals (1 mg/ml) and 2 ml of a solution of 1 mg/ml TGF-β3 in water are incubated at 50° C. for 5 days. Capillary isoelectric focusing zone electrophoresis measurements are performed before and after the temperature stress. A decrease of the TGF-β3 main peak is measured for the sample of TGF-β3 soluted in water and only a lower decrease in the TGF-β3 main peak is measured for the suspension of TGF-β3 T micro crystals.

2 ml of a suspension of H form TGF-β3 micro crystals (1 mg/ml) and 2 ml of a solution of 1 mg/ml TGF-β3 in water are incubated at 50° C. for 5 days. Capillary isoelectric focusing zone electrophoresis measurements are performed before and after the temperature stress. A decrease of the TGF-β3 main peak is measured for the sample of TGF-β3 soluted in water and only a lower decrease in the TGF-β3 main peak is measured for the suspension of TGF-β3 H micro crystals.

These results show that TGF-β3 in crystal form is more stable towards chemical degradation than TGF-β3 in solution.

EXAMPLE 10

Physical Stability of TGF-β3 Crystals T and H

A suspension of T micro crystals of TGF-β3 (10 μg/ml TGF-β3) is incubated for 5 days at 37° C. in glass or plastic vials. HPLC analysis of TGF-β3 content of these samples shows no change in TGF-β3 concentration after 5 days incubation at 37° C. In a parallel experiment under identical conditions samples of TGF-β3 soluted in water (10 μg/ml) loose between 80 and 90% of TGF-β3 due to TGF-β3 binding to the wall of the glass or plastic vials.

A suspension of H micro crystals of TGF-β3 (10 μg/ml TGF-β3) is incubated for 5 days at 37° C. in glass or plastic vials. HPLC analysis of TGF-β3 content of these samples shows no change in TGF-β3 concentration after 5 days incubation at 37° C. In a parallel experiment under identical conditions samples of TGF-β3 soluted in water (10 μg/ml) loose between 80 and 90% of TGF-β3 due to TGF-β3 binding to the wall of the glass or plastic vials.

DEPOSITION OF MIRCRORGANISMS

The following microorganism was deposited with the Deutsche Sammlung von Mikroorganismen (DSM), Mascheroder Weg 1b, D-3300 Braunschweig (FRG):

| microorganism | deposition date | accession number |
|---|---|---|
| E. coli LC 137/pPLMu.hTGF-β3 | November 28, 1989 | DSM 5658 |

What is claimed is:

1. A composition consisting essentially of Transforming Growth Factor-β3 (TGF-β3) crystals and a carrier, wherein said crystals belong to a triagonal or hexagonal space group.

2. A composition according to claim 1, in which the hexagonal space group is hexagonal crystal form H.

3. A composition according to claim 1, in which the trigonal space group is trigonal crystal form T.

4. A method for preparing Transforming Growth Factor β3 (TGF-β3) in crystalline form comprising:
   (a) combining a crystallization buffer solution comprising soluted TGF-β3 with a precipitating agent selected from a water-miscible organic solvent and polyethylene glycol to form a mixture, wherein the concentration of said precipitating agent is initially lower than that required for crystal formation;
   (b) increasing the concentration of the precipitating agent in the mixture to a level such that crystal formation will occur;
   (c) incubating the mixture of step (b) for a time and under conditions effective to produce crystals of TGF-β3; and
   (d) recovering the resulting TGF-β3 crystals from the mixture of step (c).

5. The method of claim 4 characterized in that the water miscible organic solvent is dioxane.

6. The method of claim 4 characterized in that the precipitating agent is polyethylene glycol.

7. A method for preparing Transforming Growth Factor β3 (TGF-β3) in crystalline form comprising
   (a) combining a crystallization buffer solution comprising soluted TGF-β3 with a precipitating agent selected from a water-miscible organic solvent and polyethylene glycol to form a mixture, wherein the concentration of said precipitating agent is initially lower than that required for crystal formation;
   (b) increasing the concentration of the precipitating agent in the mixture to a level such that crystal formation will occur;
   (c) adding seed crystals of TGF-β3 to facilitate TGF-β3 crystal formation in the mixture of step (b)
   (d) incubating the mixture of step (c) for a time and under conditions effective to produce crystals of TGF-β3; and
   (e) recovering the resulting TGF-β3 crystals from the mixture of step (d).

8. The method of claim 7 in which the crystallization buffer solution is seeded with microcrystal seeds of TGF-β3.

9. The method of claim 7 in which the crystallization buffer solution is seeded with macrocrystal seeds of TGF-β3.

* * * * *

UNITED STATES PATENT AND TRADEMARK OFFICE
CERTIFICATE OF CORRECTION

PATENT NO.    : 6,294,656 B1
DATED         : September 25, 2001
INVENTOR(S)   : Mittl et al.

It is certified that error appears in the above-identified patent and that said Letters Patent is hereby corrected as shown below:

Column 17,
Line 4, should read -- said crystals belong to a trigonal or hexagonal space group. --.
Line 24, should read -- The method of claim 4 wherein the water --.

Column 18,
Line 1, should read -- The method of claim 4 wherein the --.
Line 20, should read -- The method of claim 7 wherein the crystallization --.
Line 22, should read -- The method of claim 7 wherein the crystallization --.

Signed and Sealed this

Second Day of July, 2002

Attest:

Attesting Officer

JAMES E. ROGAN
Director of the United States Patent and Trademark Office